US010758953B2

(12) United States Patent
Rudser

(10) Patent No.: US 10,758,953 B2
(45) Date of Patent: Sep. 1, 2020

(54) CONNECTION SYSTEM WITH CLEANING

(71) Applicant: HeartWare, Inc., Miami Lakes, FL (US)

(72) Inventor: John Rudser, Miami, FL (US)

(73) Assignee: HeartWare, Inc., Miami Lakes, FL (US)

(*) Notice: Subject to any disclaimer, the term of this patent is extended or adjusted under 35 U.S.C. 154(b) by 488 days.

(21) Appl. No.: 15/224,744

(22) Filed: Aug. 1, 2016

(65) Prior Publication Data
US 2017/0028444 A1    Feb. 2, 2017

Related U.S. Application Data

(60) Provisional application No. 62/199,580, filed on Jul. 31, 2015.

(51) Int. Cl.
| B08B 11/00 | (2006.01) |
| B08B 1/00 | (2006.01) |
| H04N 5/765 | (2006.01) |
| H04N 5/225 | (2006.01) |
| H04N 5/232 | (2006.01) |
| G06K 7/14 | (2006.01) |
| H01R 43/00 | (2006.01) |
| A61B 90/94 | (2016.01) |
| A61B 90/96 | (2016.01) |
| A61B 90/70 | (2016.01) |
| A61M 1/12 | (2006.01) |

(Continued)

(52) U.S. Cl.
CPC .............. *B08B 11/00* (2013.01); *A61B 90/70* (2016.02); *A61B 90/94* (2016.02); *A61B 90/96* (2016.02); *B08B 1/00* (2013.01); *G06K 7/1443* (2013.01); *H01R 43/002* (2013.01); *H04N 5/2256* (2013.01); *H04N 5/23212* (2013.01); *H04N 5/765* (2013.01); *A61B 90/30* (2016.02); *A61B 90/361* (2016.02); *A61B 2218/002* (2013.01); *A61M 1/122* (2014.02)

(58) Field of Classification Search
CPC ... H04N 5/2256; H04N 5/23212; H04N 5/765
See application file for complete search history.

(56) References Cited

U.S. PATENT DOCUMENTS

| 7,213,603 B2 | 5/2007 | Pinsky |
| 8,252,247 B2 | 8/2012 | Ferlic |
| 8,296,898 B1 | 10/2012 | Moncrief |

(Continued)

FOREIGN PATENT DOCUMENTS

CN    203263863 U    11/2013

OTHER PUBLICATIONS

International Search Report and Written Opinion dated Oct. 19, 2016, for corresponding International Application No. PCT/US2016/044999; International Filing Date: Aug. 1, 2016 consisting of 9-pages.

(Continued)

*Primary Examiner* — Mikhail Kornakov
*Assistant Examiner* — Ryan L. Coleman
(74) *Attorney, Agent, or Firm* — Christopher & Weisberg, P.A.

(57) ABSTRACT

A connector cleaning system includes (a) one or more cleaning elements adapted to engage a connector and remove contaminants from a contact portion of the connector and (b) an image processing device adapted to capture an image of the contact portion after removal of contaminants.

14 Claims, 8 Drawing Sheets

(51) Int. Cl.
  *A61B 90/00* (2016.01)
  *A61B 90/30* (2016.01)

(56) References Cited

U.S. PATENT DOCUMENTS

| | | |
|---|---|---|
| 8,378,324 B2 | 2/2013 | Gardner, III |
| 8,777,504 B2 | 7/2014 | Shaw et al. |
| 2007/0289606 A1 | 12/2007 | Abrahamian et al. |
| 2010/0000040 A1 | 1/2010 | Shaw et al. |
| 2010/0296968 A1 | 11/2010 | Cady |
| 2011/0023885 A1 | 2/2011 | Vazales et al. |
| 2011/0064512 A1 | 3/2011 | Shaw et al. |
| 2011/0284024 A1 | 11/2011 | Trebella et al. |
| 2012/0016377 A1 | 1/2012 | Geroy |
| 2012/0083818 A1 | 4/2012 | Pandey |
| 2012/0195807 A1 | 8/2012 | Ferlic |
| 2012/0315201 A1 | 12/2012 | Ferlic et al. |
| 2013/0229650 A1 | 9/2013 | Wilson |
| 2013/0323117 A1 | 12/2013 | Ma et al. |
| 2013/0323119 A1 | 12/2013 | Alwan |
| 2013/0323120 A1 | 12/2013 | Ma |
| 2014/0053871 A1 | 2/2014 | Ma et al. |

OTHER PUBLICATIONS

China National Intellectual Property Administration, Chinese Office Action dated Nov. 5, 2019 for corresponding Application No. 201680045167.7, 11 pages.

CONNECTION SYSTEM WITH CLEANING

CROSS-REFERENCE TO RELATED APPLICATION

The present application claims the benefit of the filing date of U.S. Provisional Application No. 62/199,580, filed Jul. 31, 2015, the disclosure of which is hereby incorporated herein by reference.

BACKGROUND OF THE INVENTION

The present invention relates to the cleaning of a connector for use with a medical device implanted within an animal; or, more particularly, for use with a connector that is attached to a ventricular assist device ("VAD") and implantable within a living body.

The heart is sometimes incapable of providing sufficient pumping capacity to meet the needs of the body. The effects of this inadequacy can be alleviated by providing a VAD with a mechanical pump adapted to supplement the pumping action of the heart. The pump, like all other elements of the VAD, preferably has the ability to be implanted in a living body for an extended period of time while the patient is awaiting a suitable donor for a heart transplant.

U.S. Pat. Nos. 7,575,423, 7,976,271, 8,007,254, and 8,419,609, the disclosures of which are hereby incorporated by reference, disclose certain rotary blood pumps which can be used as ventricular assist devices. These pumps are electrically powered. Typically, these and other electrically powered implantable pumps are connected through a cable or wire (either being a "driveline") to a control device that supplies electric power to the pump and controls its operation. The control device must usually provide continuous electric power over the driveline. This power must be provided at relatively high current (0.5-2.0 Amps) and moderate voltage (3-40 Volts) for extended periods of time, such as years or decades, without losing electrical continuity or creating resistive heat losses that would cause physiological complications.

Each driveline may have one or more electrical connectors. For example, one end of the driveline may be attached to an electrical connector while the other end is attached to the control device. Multiple connector types may be used. For example, an exemplary set of male and female connectors is disclosed in U.S. Provisional Patent Application No. 62/093,208 (the "'208 Application), the disclosure of which is hereby incorporated by reference. Each of these connectors has a contact portion arranged to transmit electricity through the driveline when aligned with a corresponding contact portion on another mating connector. The male contact portion is on a connector shaft; whereas the female contact portion is in a connector bore.

For the VAD to perform effectively over time, the respective contact portions of each connector must remain free of contaminants such as interstitial fluid or blood. The risk of contamination is greatest during the initial implantation procedure and any subsequent replacement or upgrade procedures. For example, a connector may be moved through a tunnel in the body during one of these procedures. The contact portion of the connector may become contaminated by contacting blood in the tunnel. Because the connector may still be attached to an implanted control device, these contaminants must be typically removed in the operating room during the procedure. A technician is usually present to manually clean the contacts and document the cleaning.

These manual efforts can be very time consuming. This additional time increases the risk of unwanted complications by keeping the patient in surgery and medicated longer than might otherwise be required. Moreover, this additional time also increases the cost of the procedure by requiring every other member of the surgical team, including the operating surgeon, to stand by while the technician manually cleans the connector and documents the cleaning. If more than one implanted connector must be cleaned, which is often the case, then the amount of idle time will be increased proportionately. To alleviate these concerns, the technician may need to work in a rapid fashion, thereby increasing the risk of implanting an imperfectly cleaned connector. These additional time pressures may also render it difficult to control and document the cleaning.

The aforementioned concerns are not limited to medical procedures. Numerous other technologies also utilize similar connectors and drivelines to transmit electricity between electrical devices and control elements within a contaminant laden environment. For example, the respective contact portions of many connectors designed for aviation, marine, or other outdoor use must also remain free of contaminants, such as dirt, saltwater and living organisms. Furthermore, the safety and uptime requirements associated with these uses may also necessitate similar cleaning and documentation efforts, either of which can be similarly frustrated by time pressures.

Further improvements are required.

BRIEF SUMMARY OF THE INVENTION

One aspect of the present invention is a connector cleaning system comprising of one or more cleaning elements and an image processing device. The system may, for example, be used to clean an implantable connector, male or female, during an implantation procedure. Each cleaning element is preferably adapted to remove contaminants from at least a portion of the connector during a cleaning cycle. A cleaning medium and a drying agent are among the one or more cleaning elements that may be used to clean the connector. Each of these cleaning elements is preferably distributed about the connector within one or more chambers formed in the device. Various means for distributing the cleaning elements are described herein.

Another aspect of the present invention is an image processing device adapted to capture one or more images of the connector and transmit each image to another device. The image processing device may have a camera, a control circuit, a storage medium, and a transmitter. For example, at one or more points during a medical procedure, such as before and after the step of moving the connector through a tunnel formed in the body, said control circuit may direct the camera to capture an image or video (either an "image" in any format) of the connector. The image may be stored in the storage medium, at least temporarily, and then transmitted to another device by a transmitter. A technician may then place the image in a quality control or "QC" record that associates the image with a particular procedure.

Yet another aspect is an image processing device that is further configured to create the QR record. For example, an indicia marker may be placed on each connector to communicate identifying information about the connector. The marker may be a bar code, QR code, or other graphically transmitted and/or machine readable code placed on a camera facing portion of the connector. The image processing device may be further configured to locate the indicia marker in the image, decode the identifying information, associate the image with said information in a QC record, and transmit the QC record to another device.

Still other aspects of the present invention are methods and kits for using, assembling, and maintaining the various embodiments described herein.

BRIEF DESCRIPTION OF THE DRAWINGS

A more complete appreciation the present invention and the various advantages thereof can be realized by reference to the following drawings.

DETAILED DESCRIPTION

Although described with reference to a system for cleaning electrical connectors, it is to be understood that concepts and novelty underlying the present invention could be utilized to clean any type of device. For example, the various chambers, indicia markers, and image processors described below may be used to clean any connector used with an implantable device, or any implementation tool used to implant said device, including any instrument that is commonly used in the operating room during a medical procedure. Moreover, although described in connection with a medical procedure, such as VAD implantation, the present invention may be used to remove any type of contaminants from any type of connector in any procedure having similar cleaning and verification requirements. For example, the described system may be used to clean electrical connectors used in aviation, marine, or other outdoor environments, and to verify the cleaning of said connectors.

Figure 1:
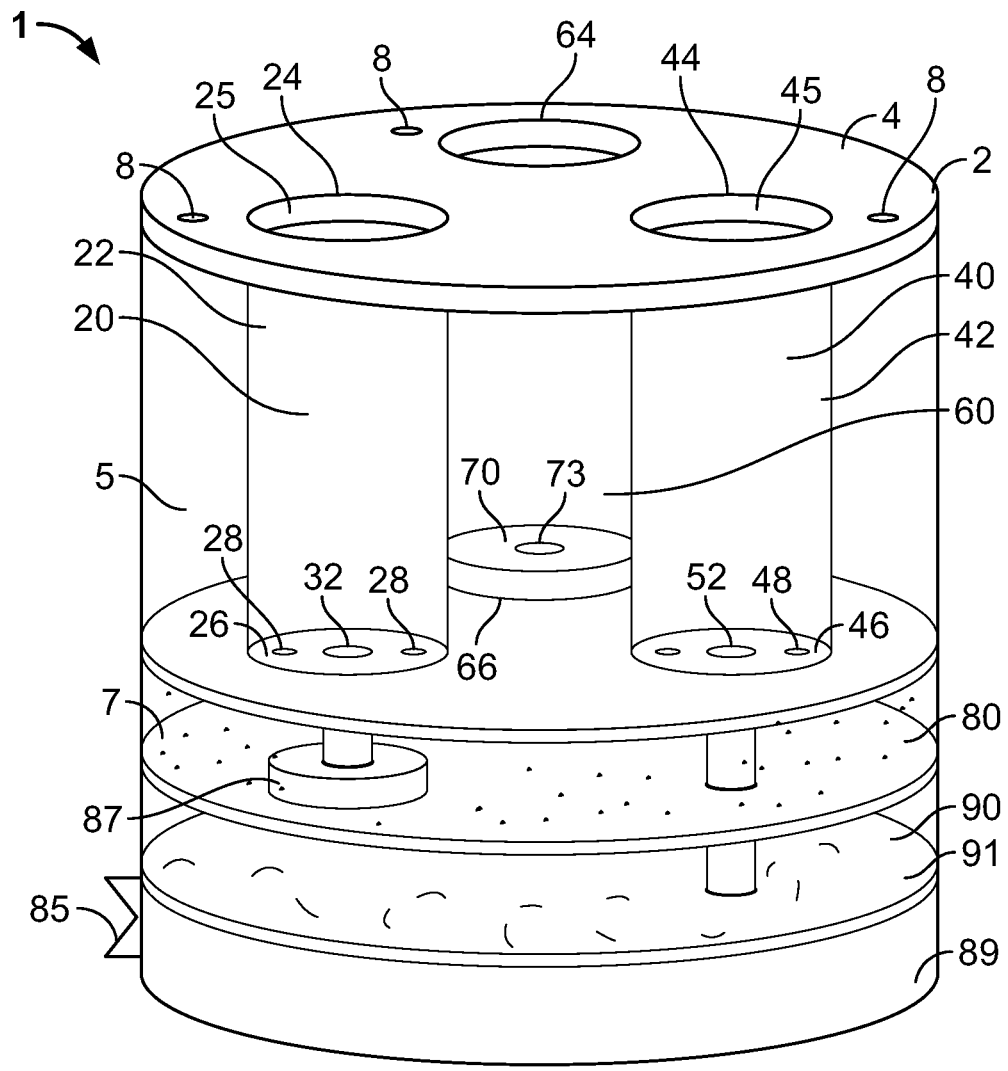
FIG. 1 provides a perspective view of an exemplary embodiment of the present invention having three chambers.

An exemplary cleaning system 1 is depicted in FIG. 1 as having an exterior housing 2 with a cleaning chamber 20, a drying chamber 40, and a verification chamber 60. Housing 2 is shown as a transparent element having a top surface 4 disposed opposite of a bottom surface 6. One or more status indicators 8 are preferably located on top surface 4. Chambers 20, 40, and 60 extend downward from top surface 4 into an interior cavity 5 formed in exterior housing 2. Although shown as a transparent element in FIG. 1, exterior housing 2 is preferably a unitary body made of polymeric, metallic, or other shapeable material that may be sterilized. It need not be transparent. Any forming or molding techniques may be used to make housing 2. The material composition of and techniques of manufacture for housing 2 may depend upon whether system 1 is intended to disposable or reusable. For example, a reusable embodiment of housing 2 may be formed from a sheet of aluminum or like metal, whereas a disposable embodiment of housing 2 may be molded from a quantity of acrylonitrile butadiene styrene ("ABS") or like material.

Figure 6:
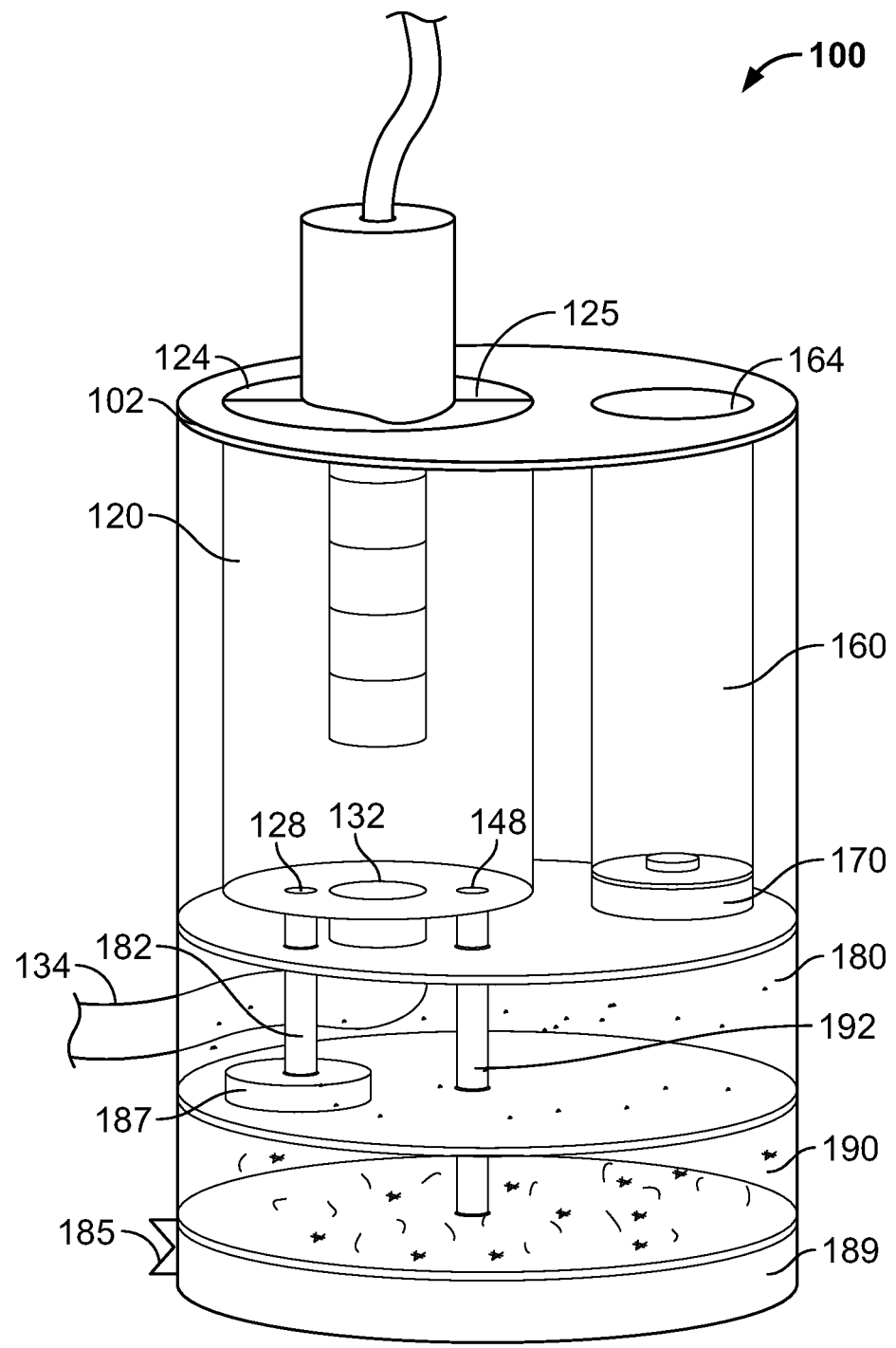
FIG. 6 provides a perspective view of an exemplary embodiment of the present invention having two chambers.
Figure 7:
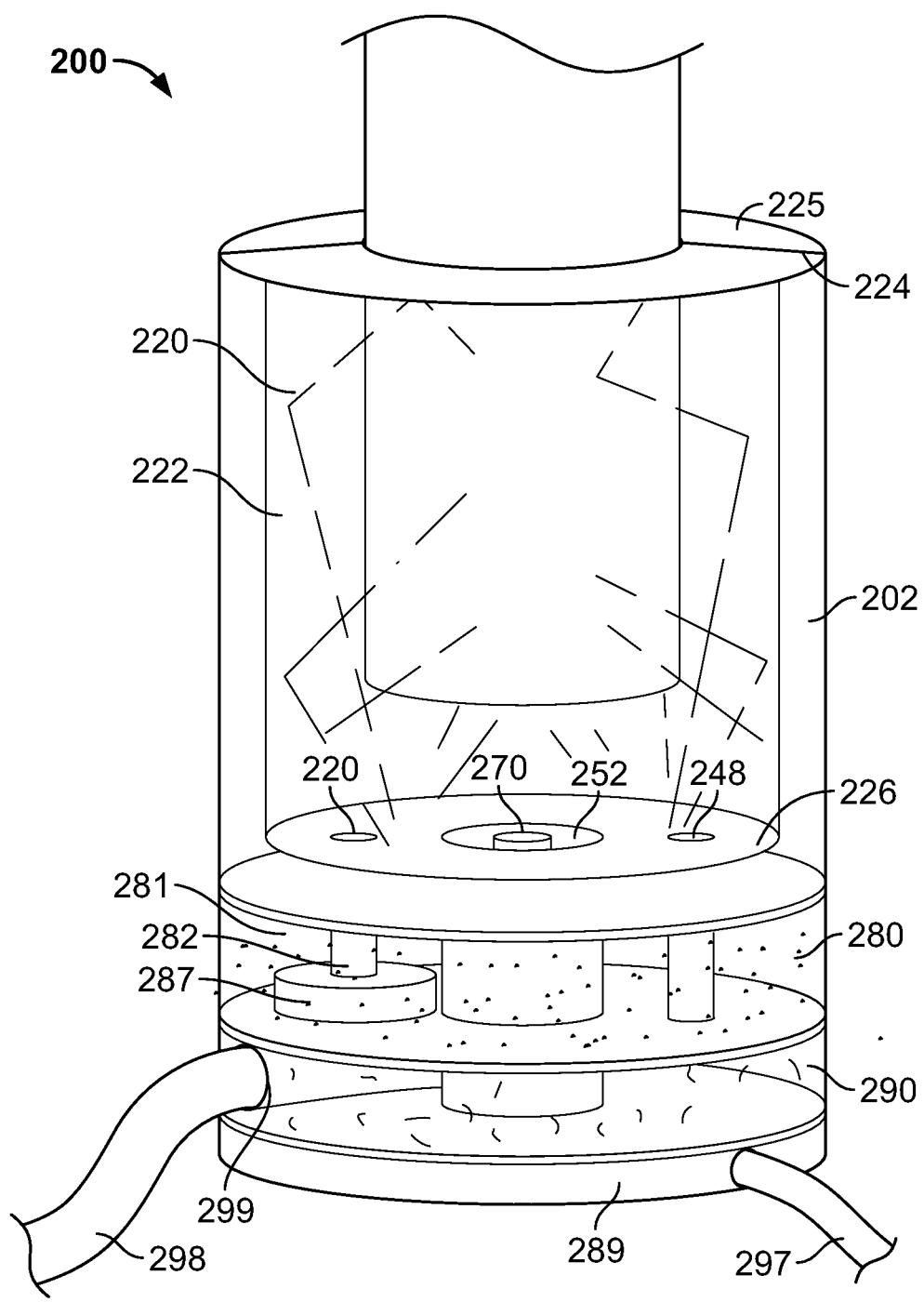
FIG. 7 provides a perspective view of an exemplary embodiment of the present invention having one chamber.

Each chamber 20, 40, and 60 is sized to receive at least a part of a connector, male, female or otherwise. Each chamber may be sized to receive either the shaft of a male connector (FIG. 6) or the bore of a female connector (FIG. 7). In FIG. 1, chambers 20, 40, and 60 are assembled together in a triangular configuration to permit ready movement of the connector in and out of each chamber within a cleaning cycle. Each of the chambers 20, 40, and 60 preferably extends into only a portion of interior cavity 5 so as to define a storage bay 7 in exterior housing 2. Bay 7 is preferably configured to receive and store the one more cleaning elements. A power source 89 is adjacent bay 7 in FIG. 1.

Figure 2:
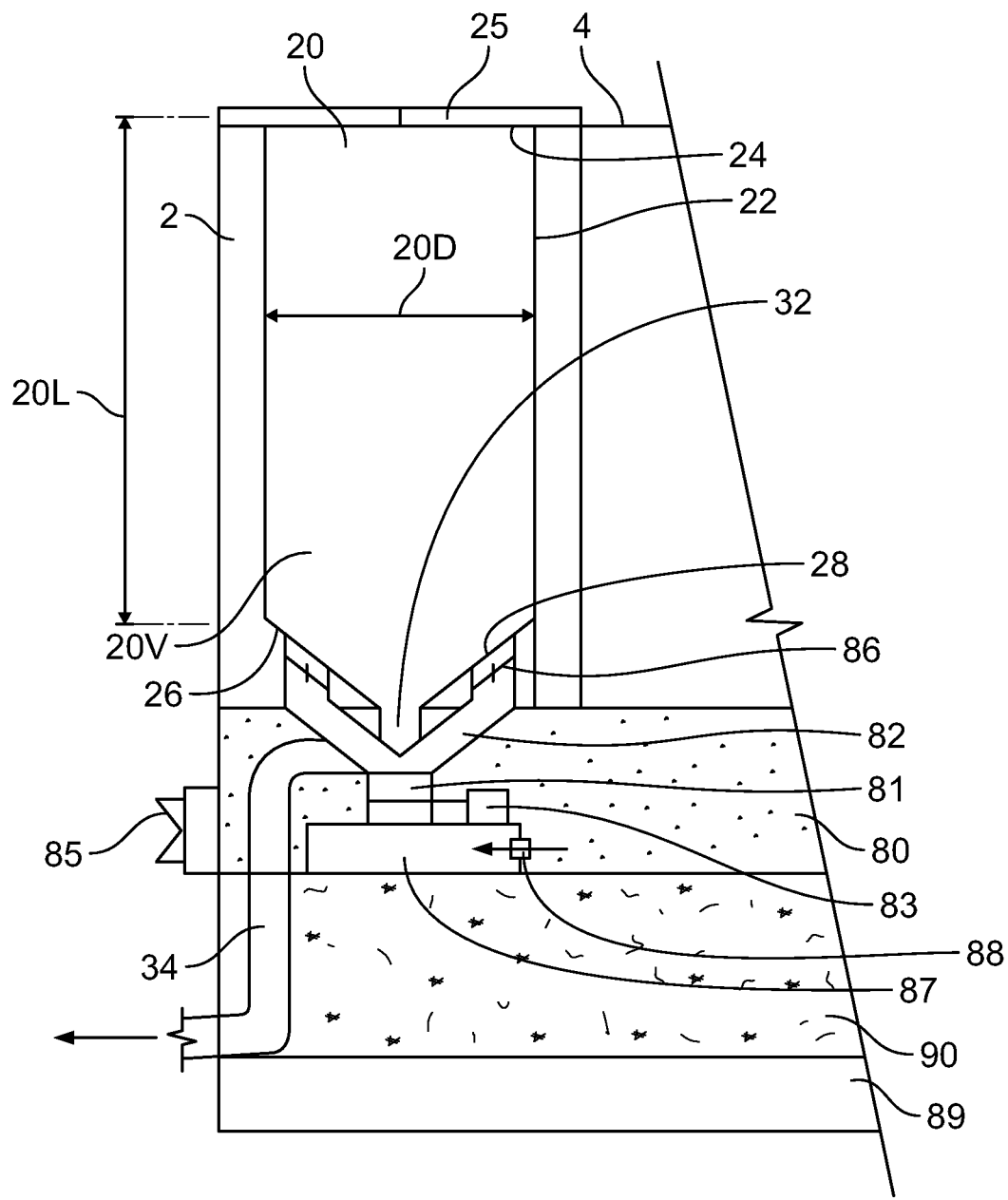
FIG. 2 provides a section view of one of the three chambers of the embodiment of FIG. 1.

Cleaning chamber 20 is a cleaning element that extends through the top surface 4 of housing 2. As shown in FIG. 2, chamber 20 has an interior surface 22 extending between an entry opening 24 and a base surface 26. Opening 24 and interior surface 22 are shown with a common dimension, shown in FIG. 2 as a cleaning chamber diameter 20D. Interior surface 22 spans along a cleaning chamber length 20L to define a cleaning chamber volume 20V. Diameter 20D and length 20L are preferably larger than the corresponding outer dimension of the largest connector to be cleaned, typically the female connector. By way of example, chamber volume 20V may be approximately 100 to 1,000 percent larger than the corresponding fluid displacement volume of a particular connector.

A sealing element 25 is preferably attached to entry opening 24. Element 25 desirably prevents the contents of chamber 20 from escaping. In FIGS. 1-2, sealing element 25 is illustrated as a split seal with at least two divided portions made of a resilient material that biases each divided portion toward the other in a sealed position. Element 25 may, for example, be adapted conform around the exterior surfaces of the connector to form a physical seal that prevents the contents of chamber 20 from escaping. For example, in FIG. 6, the male connector has a shaft that terminates in a larger base element attached to a driveline. The divided portions 25 of sealing element 25 are adapted to conform around the perimeter of the shaft, the base element, or the driveline (e.g., FIG. 6). Alternatively, the entire male connector may be pushed into chamber 20 so that divided portions of seal 25 conform around the driveline, thereby allowing the entire connector to be cleaned. Alternatively, if a female connector is to be cleaned, then sealing element 25 may conform around the outer perimeter of any portion of the female connector or its driveline (e.g., FIG. 7).

Cleaning chamber 20 preferably has one or more entry ports 28 adapted to receive the cleaning medium. System 1 of FIGS. 1-2, for example, has two entry ports 28 on base surface 26. Each port 28 receives the cleaning medium from the cleaning source portion 80 of bay 7, wherein the medium may be fed or stored. For example, ports 28 of FIG. 2 are attached to a nozzle portion 82 that comprises a plurality of conduits spanning between each entry port 28 and cleaning source portion 80. A nozzle 86 is mounted to nozzle portion 82. Nozzle 86 may be adapted to distribute a particular cleaning medium into chamber 20 in a particular direction or form. For example, as noted below, the cleaning medium may be a compressed liquid that is distributed into chamber 20 by nozzle 86 as a high pressure spray. Each nozzle portion 82 also has a valve 81 that is operated by a valve actuator 83. Valve 81 may be a butterfly valve. Actuator 83 may be an electric linear actuator that is electrically connected to power source 89 and a switching element 85 used to open or close valve 81.

An exemplary cleaning source portion 80 is depicted in FIGS. 1-2 as a sealed interior volume within bay 7. Nozzle portion 82 preferably extends into cleaning source portion 80 from base surface 26. In FIG. 2, valve 81 divides cleaning chamber 20 from nozzle portion 82. When open, valve 81 may be used to distribute the cleaning medium into chamber 20 through nozzle portion 82 from source portion 80. Portion 82 is also configured such that, when valve 81 is open, the cleaning medium may be delivered into source portion 80 through entry port 28.

Various means for expelling the cleaning medium from cleaning source portion 80 into cleaning chamber 20 are contemplated. For the embodiment of FIG. 1, switching element 85 is operated to move valve 81 into the open position and release a cleaning medium that has been pressurized within portion 80. Switching element 85 may be operated manually by the technician or automatically by a sensor, as described below. A force may be used to expel the cleaning medium. For example, switching element 85 may be operated to apply a distribution force to the cleaning medium that expels it from chamber 20. The distribution force may be applied by a device that is electrically connected to switching element 85 and power source 89. In FIGS. 1-2, for example, a pumping element 87 is used to push the cleaning medium out of cleaning source portion 80 when valve 81 is in the open position. Element 87 may be an electric pump with an impeller mounted inside of a pump housing 88 on the bottom surface portion 80. Preferably, switching element 85 is operated, manually or automatically, so as both move valve 81 into the open position and cause pumping element 87 to push the cleaning medium into chamber 20 within a cleaning cycle.

As shown in FIG. 2, cleaning chamber 20 also has one or more exit ports 32 adapted to remove the cleaning medium and any contaminants from chamber 20 (together, "waste"). At least a portion of base surface 26, such as a perimeter portion, is preferably sloped to funnel the flow of waste from chamber 20 into at least one of the exit ports 32. Each exit port 32 may be connected to a waste removal element 34, such as a conduit within exterior housing 2 that directs the waste into an external disposal reservoir, transport container, or drain.

Figure 3:
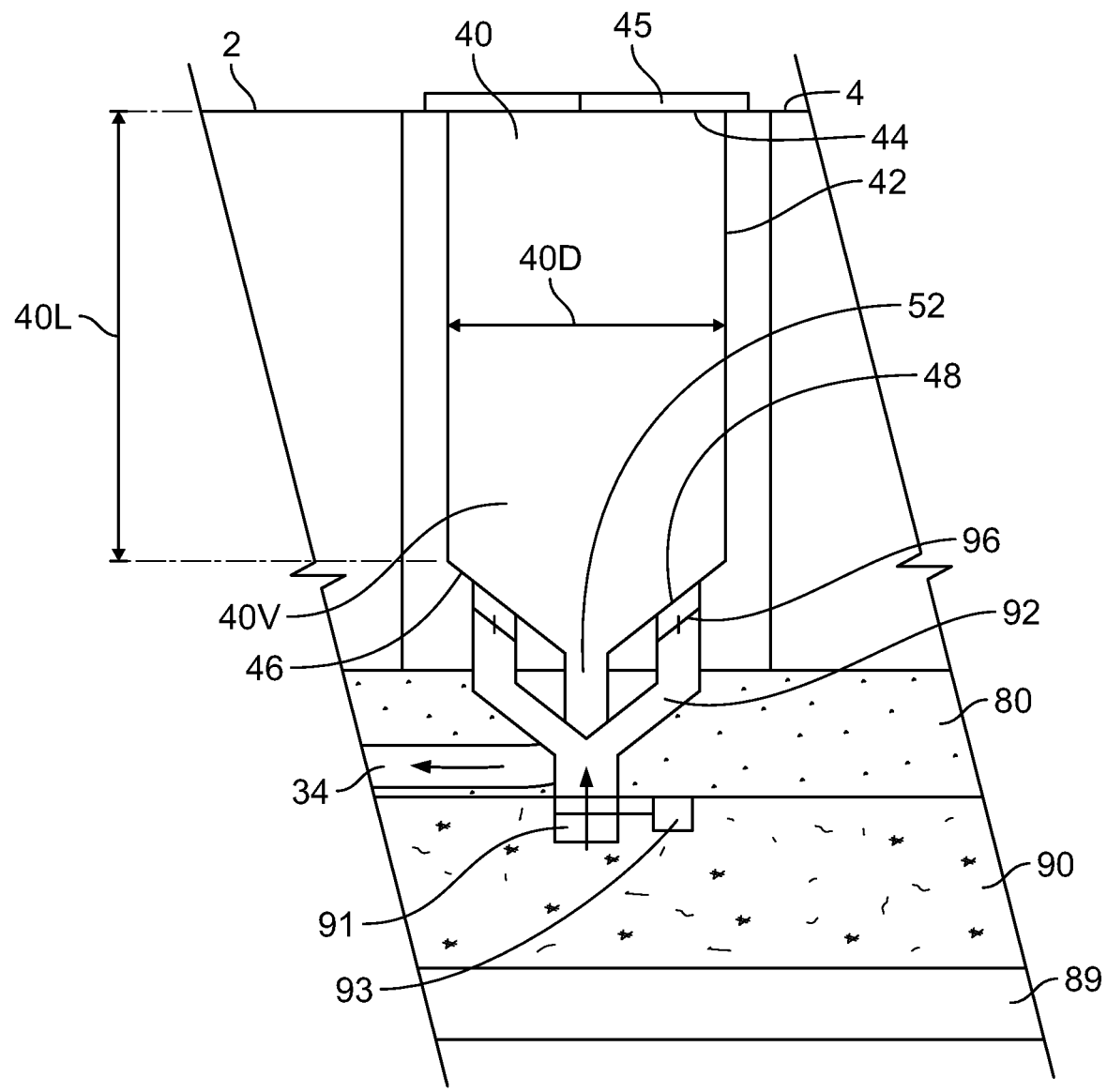
FIG. 3 provides a section view of another one of the three chambers of the embodiment of FIG. 1.

Drying chamber 40 is another cleaning element adapted to receive a male or female connector. An exemplary drying chamber 40 is shown in FIGS. 1 and 3 as having an interior surface 42 that extends through top surface 4 of exterior housing 2 from an entry opening 44 to a base surface 46. Drying chamber 40 may be dimensionally similar to cleaning chamber 20. For example, as shown in FIG. 3, chamber 40 has a drying chamber diameter 40D, length 40L, and volume 40V that are preferably equal to cleaning chamber diameter 20D, length 20L, and volume 20V. Thus, similar connectors may be received in either of chambers 20 or 40. Drying chamber 40 also has a sealing element 45 that, like sealing element 25, allows chamber 40 to be physically sealed around any portion of a connector.

Drying chamber 40 has one or more entry ports 48 adapted to receive the drying agent. Two entry ports 48 are located on base surface 46 in FIGS. 1 and 3. Each entry port 48 receives the drying agent from a drying source portion 90 of bay 7, wherein the drying agent may fed or stored. Either port 48 may be attached to a nozzle portion 92 that, similar to above, comprises a plurality of conduits spanning between entry ports 48 and cleaning source portion 90. A nozzle 96 is mounted in nozzle portion 92 in FIG. 3. Nozzle 96, similar to nozzle 86, may be adapted to distribute a particular drying agent into chamber 40 in a particular form. For example, the drying agent may be a compressed gas that is distributed into chamber 40 by nozzle 96 as a high-velocity stream. Each nozzle portion 92 also has a valve 91 with a valve actuator 93 adapted to move valve 91 between an open and closed position. Actuator 93 may, for example, be another electric linear actuator that is electrically connected to power source 89 and switching element 85 and, which may be activated to open or close valve 91.

An exemplary drying source portion 90 is depicted in FIGS. 1 and 3 as another sealed interior volume within bay 7. Nozzle portion 92 preferably extends into portion 90 from base surface 48. As shown, nozzle portion 92 extends through a part of cleaning source portion 80 due to the vertical arrangement of source portions 80 and 90. This is optional as portions 80 and 90 might be arranged in bay 7 to avoid such intrusions. Valve 91 of FIG. 3 defines the boundary between drying chamber 40 and source portion 90. When open, valve 91 may be used to either distribute the drying agent into chamber 40 from source portion 90 or place the agent in storage portion 90.

Various means of expelling the drying agent from source portion 90 are disclosed. As noted above, the preferred drying agent is a stream of compressed gas, such as air, that is distributed about the connector to remove substantial all of any remaining cleaning medium and contaminants from the connector. Accordingly, in FIG. 3, drying source portion 90 is depicted as a pressure vessel adapted to store the gas at a desired pressure, such that opening valve 91 releases the drying agent into chamber 40 through nozzle portion 92 and nozzle 96. Drying chamber 40 also has one or more exit ports 52 adapted to remove any residual cleaning medium together with any contaminants from chamber 40 (also "waste"). Each exit port 52 of chamber 40 is functionally equivalent to each exit port 32 of chamber 20. For example, each exit port 52 may also be connected to waste removal element 34.

Figure 4:
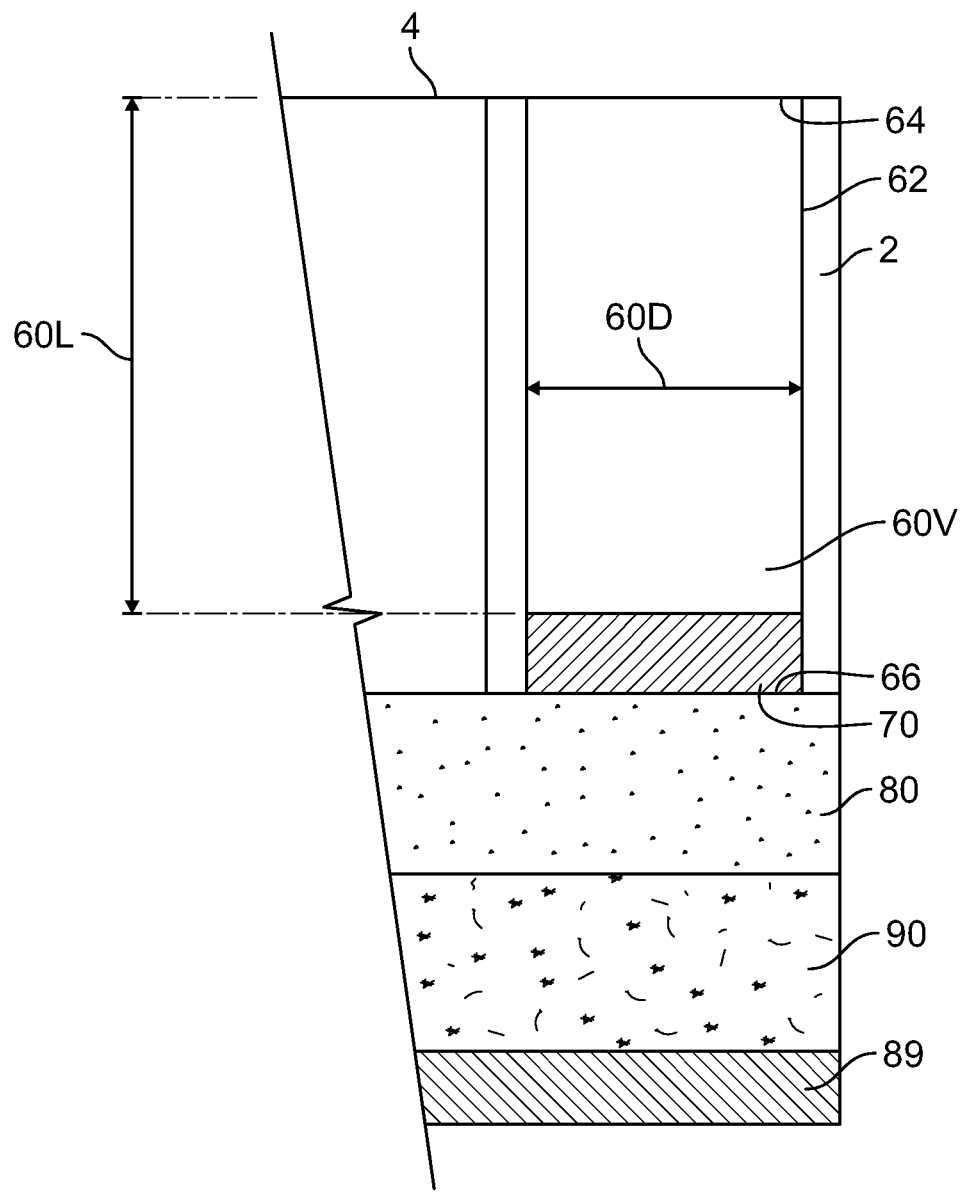
FIG. 4 provides a section view of yet another one of three the chambers of the embodiment of FIG. 1.

Verification chamber 60, like chambers 20 and 40, is also a cleaning element with an entry opening 64 that extends through top surface 4 of exterior housing 2. An exemplary chamber 60 is illustrated in FIGS. 1 and 4. As shown, chamber 60, much like chambers 20 and 40, has an interior surface 62 that extends from entry opening 64 to a base surface 66. Chamber 60 is sized similarly to chambers 20 and 40 so that the same connector may be received therein. For example, chamber 60 of FIG. 4 has a verification chamber diameter 60D and a verification chamber length 60L that are dimensionally similar to the corresponding dimensions of chambers 20 and 40. Unlike chambers 20 and 40, however, verification chamber 60 normally does not have any entry or exit ports as the various cleaning mediums and drying agents discussed herein are typically not placed in chamber 60.

Figure 5:
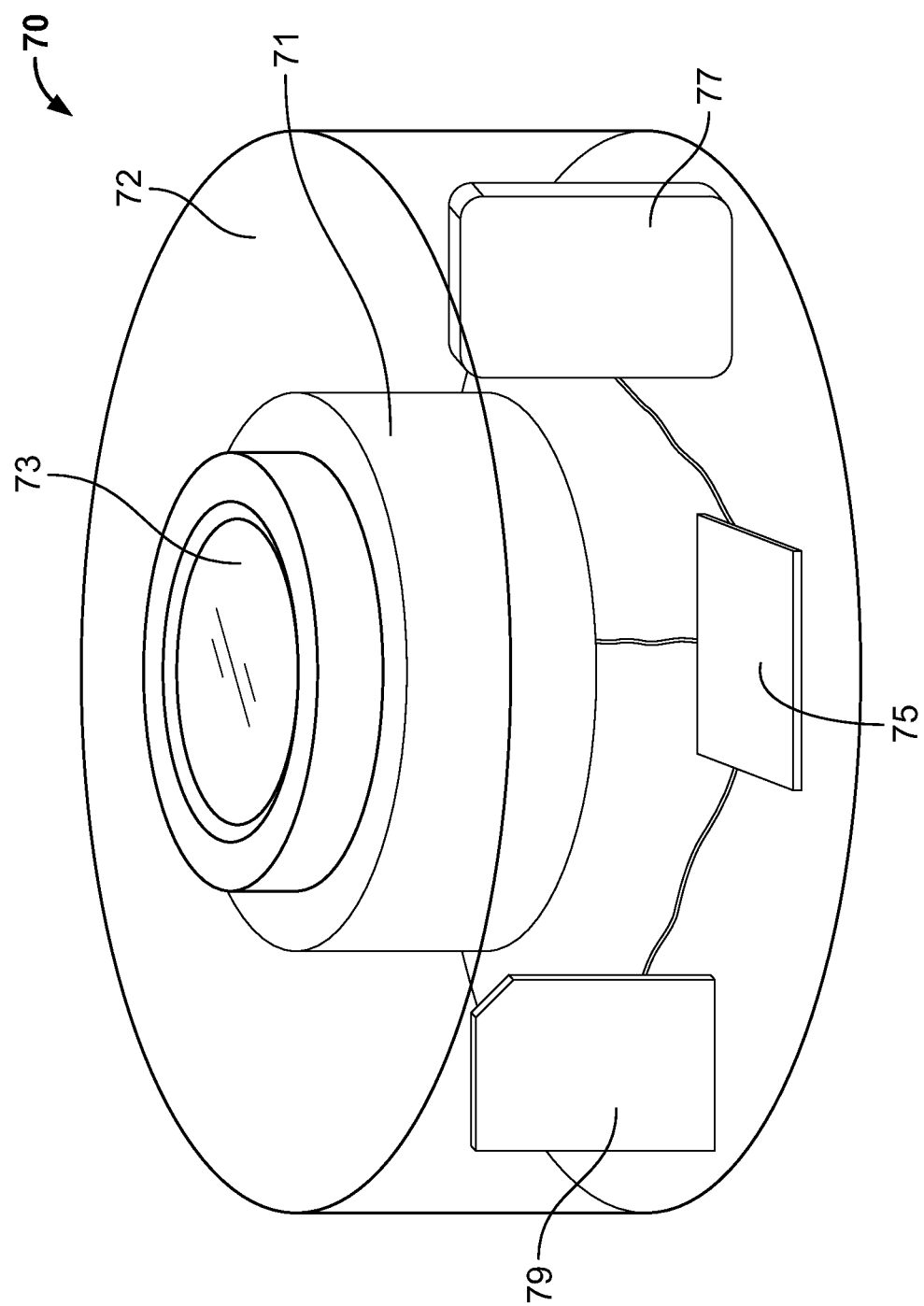
FIG. 5 provides a schematic view of one embodiment of an image processing device according to FIG. 1.

An image processing device 70 is preferably mounted on or attached to base surface 66 of verification chamber 60. Device 70 may be used to capture one or more images of a connector and transmit each image to another device. An exemplary device 70 is illustrated in FIGS. 1, 4, and 5. As shown schematically in FIG. 5, device 70 desirably has an exterior surface 72 that surrounds all of the electronic components needed to process an image; such as: a camera 71, a control circuit 75, a transmitter 77, and data storage medium 79. Each of these components is electrically connected to switching element 85 and power source 89.

Camera 71 of FIG. 5 is preferably an optical camera with a lens element 73 extending through exterior surface 72. Lens element 73 may be aligned with camera 71 and adapted to automatically focus each image. For example, lens element 73 may be a motor or tunable optical element operable with a sensor and control circuit 75 adapted to focus camera 71 on one or more portions of the connector. Camera 71 may be operable with one or more light sources that are oriented towards toward entry opening 64 so as to illuminate at least a portion of the connector for lens element 73. Storage medium 79 may be comprised of any known data storage technology, such as a secure digital card, solid-state hard drive, or like form of computer memory. Transmitter 77 may be any known transmission technology, wired or wireless, such as Wi-Fi, Bluetooth, and the like.

Control circuit 75 is illustrated conceptually in FIG. 5 as having a processor that utilizes a software program to control elements of system 1. The program may be stored on storage medium 79 and/or otherwise made available by transmitter 77. Together, power source 89, switching element 85, and control circuit 75 may be used to operate system 1. Power source 89 is preferably an internal power source, such as a lithium ion battery. In some embodiments, source 89 may be plugged in or otherwise coupled to an external power source, such as an outlet, for recharging and certain high power uses, such as those involving UV light sources. Switching element 85 is depicted in FIGS. 1-2 as one or more toggle switches on exterior housing 2. Any type of button or switch may be used. The electrical connections between switching element 85, power source 89, and any other element of the present invention, including control circuit 75, may be an interconnected set of wires.

Accordingly, control circuit 75 may be programmed to receive a command from switching element 85 and, in response, cause system 1 to perform a cleaning and/or verification cycle. For example, control circuit 75 may be configured to intermittently operate actuators 83 and 93 within a cleaning cycle. In another example, a technician may activate switching element 85 after the connector has been inserted into chamber 60. In response, control circuit 75 may initiate a verification cycle that captures an image of the connector with camera 71, stores the image in storage medium 79, and transmits the image to another device using transmitter 77. The technician may then use the other device to place the image in a QC record. Control circuit 75 may use lens element 73 to automatically focus the image, as needed. In some embodiments, control circuit 75 utilizes transmitter 77 to provide a live feed of the image that a technician can use to assess cleanliness.

Methods for using system 1 are now described, wherein the connector is moved through various cleaning and verification cycles. An exemplary method may comprise: removing contaminants from a portion of the connector during implantation of a device; and capturing an image of the said portion after the contaminants have been removed. For system 1, the removal step may further comprise: inserting the portion of the connector into a chamber; and distributing one or more cleaning elements about the portion so as to removing contaminants therefrom. Preferably, at least a contact portion of the connector is cleaned, and documented as having been cleaned, by this method.

Because system 1 has three chambers 20, 40, and 60, the removal step may comprise moving the connector in an out of the three chambers 20, 40, and 60 within a cleaning cycle. The one or more status indicators 8 on top surface 4 of exterior housing 2 may be used to coordinate such movements. In FIG. 1, for example, each indicator 8 is embodied as an LED adjacent the entry openings 24, 44, or 64 of each chamber 20, 40, and 60. Each indicator 8 may be illuminated to signal the user to move the connector into a particular chamber. Accordingly, the removal step may further comprise moving connector into one of the three chambers in response to a signal. The removal step may also comprise separate cleaning and drying steps. The cleaning step may comprise placing the connector in cleaning chamber 20 and distributing the cleaning medium about the connector so as to remove contaminants therefrom. The drying step may comprise placing the connector in drying chamber 40 and distributing the drying agent about the connector so to remove substantially all of any remaining contaminants. Each indicator 8 may be used to signal these movements, as noted above. An intermediate step may comprise activating switching element 85 to distribute either of the cleaning materials from their respective chambers 20 or 40.

For system 1, the capturing step may comprise placing the connector in verification chamber 60, obtaining an image of the connector, and transmitting the image to another device for creation of and/or placement in a QC record. Indicators 8 may be used to signal this movement as well by, for example, prompting the user to both move the connector into chamber 60 and hold said connector in chamber 60 until the image has been obtained. An intermediate step may include activating switching element 85 once the connector has been inserted into chamber 60 so as to initiate a verification cycle. One or more images may be taken in said cycle. Camera element 73 may be utilized to automatically focus each image. In some embodiments, the capturing step may further comprise placing the image in the QC record and associating the image with the connector in the QC record. For example, the technician may use system 1 to capture and transmit a plurality of images to another device. The technician may then use the other device to create the QC record and associate each image with identifying information about the connector or the procedure, such as the make and model of the connector or date, time, and location of the procedure, and the name of the technician responsible for the cleaning (individually or collectively the "identifying information").

Numerous alternate embodiments of each element of system 1 and associated methods are now described. Wherever possible, like elements have been labeled with like reference numbers, except within in an alternate series of numbers, such as 100, 200, or 300. Of course, any element described with reference to these alternative embodiments may be incorporated into any other embodiment of the present invention.

Chambers 20, 40, or 60 have been described as three separate cylinders that are dimensionally similar so that the same connector may be cycled in-and-out of each chamber. This is not required. For example, the size and portability of system 1 may be altered by modifying the spatial arrangement and geometry of chambers 20, 40, or 60. A consolidated system 100 is depicted in FIG. 6, for example, wherein the cleaning medium and drying agent are distributed within a combined cleaning-drying chamber 120 so as to reduce the size of an exterior housing 102. Chamber 120 is dimensionally equivalent to each of chambers 20 and 40 and has similar features. Base surface 126, for example, has an entry port 128 for the cleaning medium, an entry port 148 for the drying agent, and an exit port 132 for the removal of waste. Ports 128 and 148 are connected to their respective cleaning and drying source portions as above. Desirably, verification chamber 160 remains entirely separate from combined chamber 120 in system 100. Although not required, keeping chambers 120 and 160 separated prevents the image processing device 170 from being damaged by the one or more cleaning elements. Moreover, it also allows verification chamber 160 to be smaller than combined chamber 120 because no physical cleaning materials are distributed in chamber 160, thereby further reducing the size of exterior housing 102.

System 200 of FIG. 7 presents an even more consolidated embodiment of system 1, wherein a single chamber 220 is adapted to perform all of the functions of chambers 20, 40, and 60. Single chamber 220 has an interior surface 222 that extends into housing 202 between an entry opening 224 and a base surface 226. Opening 224 has a sealing element 225 similar to above. Base surface 226 may be even further adapted within system 200. For example, base surface 226 must now accommodate: an entry port 228 and an entry port 248, each being connected to their respective cleaning and drying source portions 280 and 290; an exit port 252; and an image processing device 270. Each of these elements may be arranged around a centrally located exit port 252. For example, device 270 may have a cylindrical housing 202 that is mounted coaxially within exit port 252 so that the flow of waste is drained out of single chamber 220 via the spaces formed between port 252 and device 270. Alternatively, some of these elements may be located on interior surface 222. In FIG. 7, drying source portion 290 has an opening 299 adapted to receive an external supply line 298. Power source 289 is likewise shown as being attached to a plug-in cable 297.

Elements of each chamber 20, 40, or 60 may also be modified. Cleaning chamber 20, for example, is described as having a sealing element 25. Alternatively, the shape of chamber 20 could be narrowed at entry opening 24 so as to obtain a closer fit with the connector, thereby potentially eliminating the need for sealing element 25. Cleaning chamber 20 is also described as having two entry ports 28 and one exit port 32 located on base surface 26. The exact number of and location of ports 28 or 32 in chamber 20 may be a matter of design choice. For example, any number of ports 28 or 32 may alternatively be located on either base surface 26 or interior surface 22 of chamber 20.

The cleaning medium has been described as a liquid that is stored in cleaning source portion 80 and then compelled into chamber 20 through valve 81, nozzle portion 82, and nozzle 86 by pumping element 87. Each of these elements may also be modified. Nozzle 86, for example, may comprise any nozzle type adapted to distribute the liquid in a particular direction, form, temperature, or velocity. In some embodiments, nozzle 86 may be adapted to distribute the medium onto the connector in a particular shape. The medium may, for example, be distributed by nozzle 86 in a convergent shape that increases the kinetic energy of cleaning medium so as to pressure wash the any contact portions located on the shaft of a male connector (FIG. 6). Alternatively, the medium may be distributed by nozzle 86 in a cone shape that is uniquely suited to wash over any contact portions located on the interior surfaces of a female connector bore (FIG. 7). Valve 81 has been described as a butterfly valve operated by an electric linear actuator 83. Any known valve or actuator type may be used. In some embodiments, valve 81 may be modified to eliminate the need for actuator 83. For example, valve 81 might be a pressure valve adapted to retain the cleaning medium in cleaning source portion 80 until the medium, under the influence of a distribution force, reaches a pressure that is sufficient move and move and hold valve 81 in open position. The force may be applied by pumping element 87 or like means.

Cleaning source portion 80 has been described as a sealed interior volume within bay 7. If system 1 is a stand-alone device, then portion 80 may store the cleaning medium until distribution. In other embodiments, portion 80 may be attached to an external supply of the cleaning medium, such as a supply line made of PVC or like material. Once the external supply is turned on, cleaning source portion 80 thereby serves to collect an amount of the cleaning medium before distribution into chamber 20. This configuration allows pumping element 87 to be omitted. Alternatively still, valve 81 may be omitted such that a perpetual flow of cleaning medium is distributed in chamber 20 through nozzle 86 once the external supply is turned on.

Exit port 32 has been described as an open drain. A valve and valve actuator might be used to seal exit port 32 so that cleaning chamber 20 may be filled with the cleaning medium. This configuration allows the connector to be soaked in the cleaning medium for a period of time during a cleaning cycle when said valve is closed. Chamber 20 may further comprise an aerating element that directs a flow of compressed gas through cleaning medium during the soak time. The gas may originate from drying source portion 90. Once the cleaning cycle is complete, the technician may simply open the valve to remove the waste.

A heating element may be included in any embodiment of system 1 to heat the cleaning medium and/or drying agent. The heating element may be located inside any of source portions 80 or 90, nozzle portions 82 or 92, or pump housing 88. Preferably, the heating element is an electric coil that is electrically connected to switching element 85 and power source 89, such that activation of element 85 heats the element.

Any element of drying chamber 40 that is common to cleaning chamber 20 may be likewise modified. Thus, seal 45, the shape of chamber 40, the arrangement or omission of entry and exit ports 48 and 52, or any other like elements may be modified as above. Other elements of drying chamber 40 may be further modified. Nozzle portion 92, for example, may also be modified to distribute the drying agent in a particular direction, form, temperature, or velocity. The preferred drying agent is a stream of compressed air. Thus, nozzle 96 may comprise any nozzle type adapted to distribute the stream of air in a particular direction, form, temperature, or velocity. In complement, the interior surface 42 of chamber 40 may have channels, grooves, or other guiding features adapted to enhance the drying capabilities of chamber 40. For example, these features may be aligned with the flow from nozzle 96 to cause a turbulent vortex of compressed air to flow rapidly about any connector placed therein.

Additional drying agents may be deployed within drying chamber 40. An absorbent element may, for example, be inserted into chamber 40 so as to collect any waste that is blown off of the connector during the cleaning cycle, h) other embodiments, drying chamber 40 may further comprise a light source that is adapted to extinguish microorganisms by illuminating the connector with a cleansing light. For example, an exemplary light source may be adapted flood chamber 40 with short-wavelength ultraviolet radiation (also known as UV-C). Said light source may be electrically connected to switching element 85 and power source 89. Sealing element 45 may be used to prevent the cleansing light from escaping chamber 40. Interior surface 42 may have a reflective coating adapted to distribute said cleansing light within chamber 40.

Drying source portion 90 has been described as another sealed interior volume within bay 7. In a stand-alone device, portion 90 may also be used to store the drying agent until use. Drying source portion 90 may be attached to an external supply of the drying agent, such as a compressed air or gas supply line. For example, a supply line made of PVC or like material may be attached to drying source portion 90 to deliver a pressurized amount of gas to portion 90. An exemplary supply line 297 is illustrated in FIG. 7 with respect to system 200. Alternatively, source portion 90 may be adapted to receive one or more pressurized containers of the drying agent, such as a $CO_2$ cartridge. If the pressure is positive, then nozzle portions 92 and nozzle 96 will distribute the stream of air when valve 91 is opened. Alternatively, if the air pressure is negative, then valve 91 may be omitted in favor of an exit port 52 and nozzle portion 92 that are adapted to suck the waste out of drying chamber 40 through a vacuum nozzle 96.

Alternative embodiments of verification chamber 60 and image processing device 70 are also been contemplated. For example, one or more lamps or LEDs may be mounted in chamber 60 or on image processing device 70 to illuminate the connector for camera 71. The interior surfaces 62 of chamber 60 may have a reflective coating that aids in illumination. Although camera 71 has been described as an optical camera, the present invention is not limited to any particular sensing or imaging technology. For example, camera 71 and any illuminating light sources may be adapted to capture an image of the connector using long wave ultra violet light (UV-A or UV-B) so as to better display contaminants. Multiple cameras 71 may also be deployed to capture multiple images of the connector, each having a unique perspective, form, or spectrum. Although chamber 60 is described without reference to a sealing element, entry opening 64 may utilize a sealing element, like element 25, to help position the connector for the camera and prevent the aforementioned light from escaping.

As described above, camera 71 is configured to transmit the image to another device for placement in a QC record. A technician may use the other device to associate the image with the connector in a QC record. Control circuit 75 may be further configured to automate this process. For example, each connector may have an indicia or marker located on a camera-facing portion of the connector. The indicia may be a bar code, QR code, or other graphically transmitted or machine readable code that is adapted to transmit identifying information about the connector or the procedure. For a male connector, the indicia may be located on the tip of the shaft; whereas, for a female connector, the indicia may be located on an interior surface of the bore. Control circuit 75 preferably includes a reader operative to identify and read the indicia. For example, camera 71 may be configured to capture an image of the connector that includes the indicia. Said reader may identify the indicia, decode the identifying information, create a QC record that associates each image with the identifying information, and transmit the QC record to another device. Multiple images of each connector may be used. For example, camera 71 may capture a first image of a portion of the connector that includes the indicia. Control circuit 75 may be configured to identify the location of the indicia in the first image, focus camera 71 upon said location, and take a second image of the indicia. The reader is then operated to decode the indicia from the second image. In either example, control circuit 75 is used to transmit the one or more images to another device within a QC record that associates each image with the identifying information.

Switching element 85 has been described as one or more physical switches that are electrically connected to numerous elements of the present invention. For example, one switch may be activated to distribute the cleaning medium, while another switch is activated to distribute the drying agent, and yet another switch is activated to operate device 70. Any known switching technology may be used to manually operate system 1. As noted above, switching element 85 may alternatively be operated automatically by one or more sensor located in, for example, any or all of chambers 20, 40, or 60. For example, a motion sensor may be placed in cleaning chamber 20 to determine whether or not a connector has been inserted therein. Switching element 85 may thus be operated when this motion sensor is tripped, such that the mere insertion of a connector into chamber 20 automatically causes distribution of the cleaning medium into chamber 20 through valve 81. Sealing element 25 may also have a sensor configured to operate switching element 85. For example, at least one of the divided portions of sealing element 25 may have a strain gauge that generates a signal when the divided portion is deflected upon insertion of the connector. Thus, switching element 85 may again be operated whenever a connector is disposed within chamber 20. Any known sensor may be deployed to automate switching element 85. Elements of chambers 40 and 60 may be similarly automated.

Control circuit 75 has been described as having computer processor that may be programmed to control system 1. System 1 may comprise a plurality of such processors, each being tasked with a different control functions. Each control circuit may have a local processor fed by power supply 89, or a remote processor placed in communication with system 1 via transmitter 77. In this regard, any functions described herein with reference to control circuit 75 may alternatively be performed by an additional processor, local or remote.

Consolidated systems 100 and 200 may provide still other opportunities for automation. Control circuit 175 of system 100, for example, may be programmed to alternatively distribute the respective cleaning mediums and drying agents in various forms within a cleaning cycle adapted to more aggressively clean the connector. The cleaning elements may be applied at various pressures and temperatures within this cycle. Similar benefits may be realized within system 200. For example, system 200 may alternatively comprise a single light source that is operable at a first intensity to extinguish microorganisms and a second intensity to illuminate the connector for image processing device 270. The light source may have two lamps for this purpose, such as an LED and a UV-C lamp. Control circuit 75 may also be used to activate these light sources within a cleaning cycle to further cleanse the connector.

Figure 8:
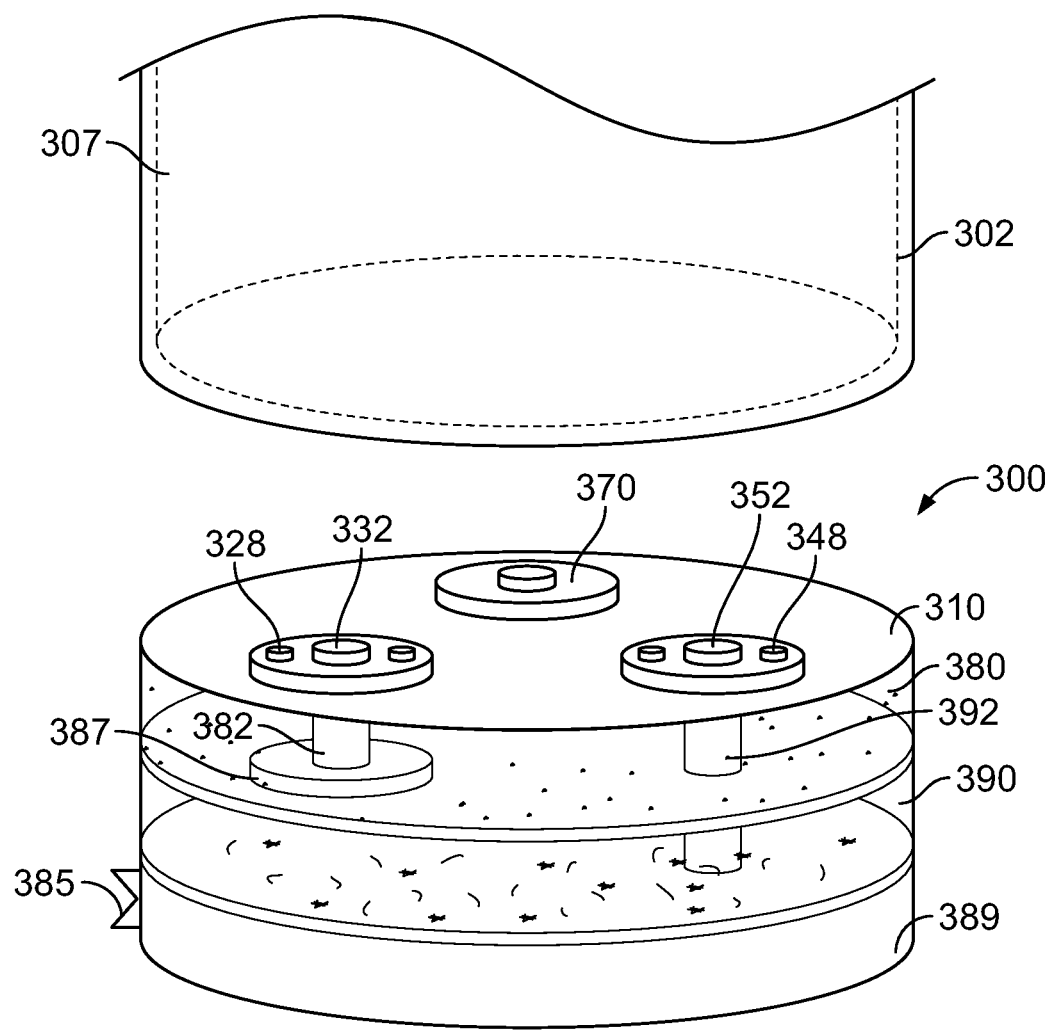
FIG. 8 provides a perspective view of an exemplary embodiment of the present invention having a removable cartridge.

Elements of an alternate system 300 are shown in FIG. 8. In contrast to system 1, the exterior housing 302 of system 300 has a storage bay 307 that is adapted to receive a cartridge 310. Each of cleaning source portion 380 and drying source portion 390 are housed in cartridge 310. Preferably, each operable element of chambers 20, 40, and 60 is incorporated into cartridge 310, such that system 300 is fully operational when cartridge 310 is placed in bay 307. In FIG. 8, for example, each of the respective entry ports 328 and 348, and exit ports 332 and 352, are part of cartridge 310. An image processing device 370 is also attached to cartridge 310. Although not shown, each of the respective base surfaces of each chamber of housing 302 preferably has a base surface opening adapted to receive one of said ports when cartridge 310 is placed bay 307. A sealing element may be placed between exterior housing 2 and cartridge 310 to prevent leakage from the base surface openings.

Numerous benefits may be derived from system 300. For example, moving the more complex elements of system 300 onto cartridge 310 allows housing 302 to be formed as a simple shell. Additionally, in system 300, each of housing 302 and cartridge 310 may be manufactured and delivered separately and of differently materials. Housing 302 may be made of re-usable material, such as aluminum, while cartridge 310 is made of disposable material, like plastic. Each of these separate elements may also be sterilized, separately or collectively. For example, housing 302 may be sterilized in the operating room, while cartridge 10 is sterilized by the manufacturing and delivered to the operating room in a sterilized container.

System 300 also provides the technician with the ability to select a particular cleaning medium and drying agent for use with a particular connector or contamination type. For example, exterior housing 302 may be delivered in a kit comprising a plurality of cleaning cartridges 310. One cartridge 310 might be configured to store the a particular cleaning medium and drying agent locally in portions 380 and 390, while another embodiment of cartridge 310 operates exclusively with external sources. Still other cartridges may be provided to vary chemical composition of the cleaning elements. For example, one cartridge 310 may be supplied with a harsh cleaner adapted to remove a particular type of contaminant, such living tissue that has grown into the exterior surface of an implanted connector, while another cartridge 310 is supplied with an alcohol or water-based cleaner that removes blood or interstitial fluid from a new connector.

Although the invention herein has been described with reference to particular embodiments, these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A connector cleaning system comprising:
one or more cleaning elements, wherein the one or more cleaning elements comprise a first chamber and the one or more cleaning elements are configured to spray fluid onto a connector in order to remove contaminants from a contact portion of the connector;
an imaging processing device adapted to capture an image of the contact portion after removal of contaminants; and
an exterior housing in which the one or more cleaning elements and the image processing device are contained, wherein the exterior housing has a second chamber in which the image processing device is disposed, and wherein the exterior housing is configured to contain cleaning medium.

2. The system of claim 1, further comprising a control circuit arranged to store the image in a storage medium.

3. The system of claim 2, further comprising a transmitter configured to send the image to another device.

4. The system of claim 2, wherein the control circuit is operative to store the image in the storage medium within a record that associates the image with the connector.

5. The system of claim 4, wherein the control circuit includes a reader operative to read indicia on the connector and associate the image with the connector by storing information read from the indicia in the record along with the image.

6. The system of claim 5, wherein the image processing device is operative to capture an image of the connector that contains the indicia and the reader is operative to read the indicia from the image.

7. The system of claim 1, wherein at least one of said one or more cleaning elements is physically connected to the image processing device.

8. The system of claim 1, further comprising a nozzle adapted to apply the cleaning medium to the connector, wherein the one or more cleaning elements are adapted to remove the cleaning medium and the contaminants after the cleaning medium has been applied.

9. The system of claim 8, further comprising a light source, wherein the connector is illuminated by the light source at least when the image is captured by the image processing device.

10. The system of claim 9, wherein the image processing device comprises at least a camera with a lens element that is operable to focus the image for the camera.

11. The system of claim 9, wherein the light source has one or more lamps operable at a first intensity to extinguish microorganisms and a second intensity to illuminate the connector for the image processing device.

12. A device implantation kit comprising:
an implantable device attached to a connector with a contact portion; and
a cleaning apparatus adapted to clean the contact portion during implantation of the device, the apparatus having:
at least one cleaning element, wherein the at least one cleaning element comprises a first chamber, and wherein the at least one cleaning element is configured to spray fluid onto the connector in order to remove contaminants from the contact portion;
a second chamber;
an exterior housing in which the first and second chambers are contained; and
at least one imaging device disposed within the second chamber, the at least one imaging device being adapted to capture an image of the contact portion after removal of the contaminants.

13. The kit of claim 12, where the cleaning apparatus further comprises a control circuit arranged to store the image in a storage medium within a record that associates the image with the connector.

14. The kit of claim 12, further comprising a quantity of liquid cleaning medium, wherein the cleaning apparatus has a nozzle with a pump adapted to apply an amount of the quantity of the liquid cleaning medium to the contact portion.

* * * * *